United States Patent [19]
Aboul-Hosn et al.

[11] Patent Number: 6,113,536
[45] Date of Patent: Sep. 5, 2000

[54] DEVICE AND METHOD OF ATTACHING A BLOOD PUMP AND TUBES TO A SURGICAL RETRACTOR

[75] Inventors: Walid N. Aboul-Hosn; William Russell Kanz, both of Sacramento; Kelly McCrystle, Healdsburg; Roland W. Ziegler, Cameron Park, all of Calif.

[73] Assignee: A-Med Systems, Inc., West Sacramento, Calif.

[21] Appl. No.: 09/164,395

[22] Filed: Sep. 30, 1998

[51] Int. Cl.⁷ .................................................. A61B 17/02
[52] U.S. Cl. ........................... 600/231; 600/227; 600/232
[58] Field of Search .................................... 600/201, 205, 600/227, 228, 231, 232, 233, 235, 204, 229

[56] References Cited

U.S. PATENT DOCUMENTS

| | | | |
|---|---|---|---|
| 2,082,782 | 6/1937 | Allen | 600/205 |
| 3,320,948 | 5/1967 | Martin | 600/205 |
| 4,337,762 | 7/1982 | Gauthier | 600/233 |
| 4,562,832 | 1/1986 | Wilder et al. | 600/205 |
| 4,605,990 | 8/1986 | Wilder et al. | 600/218 |
| 5,067,477 | 11/1991 | Santangelo | 600/227 |
| 5,167,223 | 12/1992 | Koros et al. . | |
| 5,503,617 | 4/1996 | Jako | 600/201 |
| 5,529,358 | 6/1996 | Dinkler et al. | 600/229 |
| 5,582,577 | 12/1996 | Lund et al. . | |
| 5,609,565 | 3/1997 | Nakamura | 600/229 |
| 5,697,891 | 12/1997 | Hori | 600/201 |
| 5,755,660 | 5/1998 | Tyagi . | |
| 5,772,583 | 6/1998 | Wright et al. . | |

Primary Examiner—Paul J. Hirsch
Attorney, Agent, or Firm—Jonathan Spangler

[57] ABSTRACT

A surgical retractor has a connection region to connect to cannulas, tubing, blood pumps, and the like. By fixing these items against the surgical retractor, they are kept out of the surgical field of view and thus do not interfere with the surgery.

43 Claims, 15 Drawing Sheets

DEVICE AND METHOD OF ATTACHING A BLOOD PUMP AND TUBES TO A SURGICAL RETRACTOR

BACKGROUND OF THE INVENTION

1. Field of the Invention

The invention relates generally to the field of surgical instruments, and more particularly, to surgical retractors.

2. Brief Description of the Prior Art

Surgical retractors are medical instruments which hold a patient's tissue such that the edges of a surgical incision are away from the field of surgery. Surgical retractors typically have retractor arms attached to a support shaft. The retractor arms are positioned within the surgical incision and then spread to allow an open field of surgery. An example of a prior art surgical retractor is given in Koros, et al., U.S. Pat. No. 5,167,223, which is incorporated herein by reference.

In cardiopulmonary bypass surgery (CPB) surgery, the patient's sternum is spread using a surgical retractor. This allows the surgeon access to the patient's heart to perform the necessary procedures. Typically a cannula is inserted within the patient's right atrium to withdraw blood from the patient's heart, a second cannula is placed within the patient's aorta to return blood to the patient. The cannula are connected to a blood pump which is usually placed outside the surgical field, and is connected to the patient with tubing. During surgical procedures the surgeon must insure that the cannula are not disturbed from their placement. Typically when inserting the cannula the surgeon inserts a purse string incision at the target location, inserts the cannula then pulls the purse string tight, thereby creating a seal about the diameter of the cannula. If the cannula moves or deflects to a certain degree the purse string may leak if this happens the surgeon must tighten the purse string more to eliminate the leak, it is possible that the leak may not be stoppable and the cannula must be reinserted through a new purse string at another location and the first purse string must be sutured closed. Also during bypass procedures the venous drainage line is placed within the patient's right atrium. This line drains blood from the body by gravity, therefore this line is very sensitive to placement within the atrium and any movement during the surgical procedure. This tends to complicate the surgical procedure and increase the amount of time that the patient is on the CPB circuit Additionally, movement of any of the cannula that cause the openings to become occluded results in a reduced flow rate through the CPB circuit which may cause complications in the surgical procedure.

Open heart surgery is delicate work in which the blood flow must be maintained while the procedure is performed by the surgeon on fragile blood vessels. It is desired to have an improved surgical retractor that can aid in performing this delicate work.

SUMMARY OF THE PRESENT INVENTION

The present invention generally relates to a surgical retractor having a connector allowing the connection of medical devices for transferring fluids, such as a blood pump, tubes or catheters, to the surgical retractor. In the past, even when a stabilizer is attached to the retractor to hold the heart in position, the tubes and catheters used to transfer blood during surgery had a tendency to interfere with the surgeon's operating field of view, complicating the delicate open heart surgery The tubing could also shift inadvertently during surgery, possibly touching delicate areas of the heart region or fouling the placement of the cannula. In the present invention, by connecting the tubes, catheters, and blood pump to the surgical retractor, these items are held fixed at least partially out of the surgeon's field of view during surgery.

In one embodiment of the present invention, the surgical retractor includes removable clips which are detachably attached to the retractor. The clips can hold a wide range of medical devices used to transfer fluids, such as blood, during surgery. In a preferred embodiment, the clips are easily removable and can be placed at different locations on the surgical retractor.

In one embodiment, the surgical retractor has holes for connecting to the clips. In another embodiment, the clips partially wrap-around a retractor arm of the surgical retractor.

In yet another embodiment of the present invention, the retractor has a cut-out portion on one of the arms which allows the medical device to be connected to the arm. For example, a dovetail cut can be formed into one of the arms, and a medical device for transferring fluids, such as a blood pump has a dovetail connector portion so it can be attached to the arm.

Another embodiment of the present invention comprises a connector for use with a surgical retractor. The connector comprises an element for connecting to the surgical retractor; a flexible arm and a holding means for holding a surgical instrument. The flexible arm can position the surgical instrument in a convenient location for the surgeon.

The surgical retractor embodiments of the present invention can aid in the surgeon's performing of delicate heart procedures. Further, the surgical retractor of the present invention may reduce the number of people within the operating room. Also, the surgical retractor of the present invention maximizes the amount of space available to the surgeon during open chest procedures.

DETAILED DESCRIPTION OF THE PREFERRED EMBODIMENT

Figure 1:
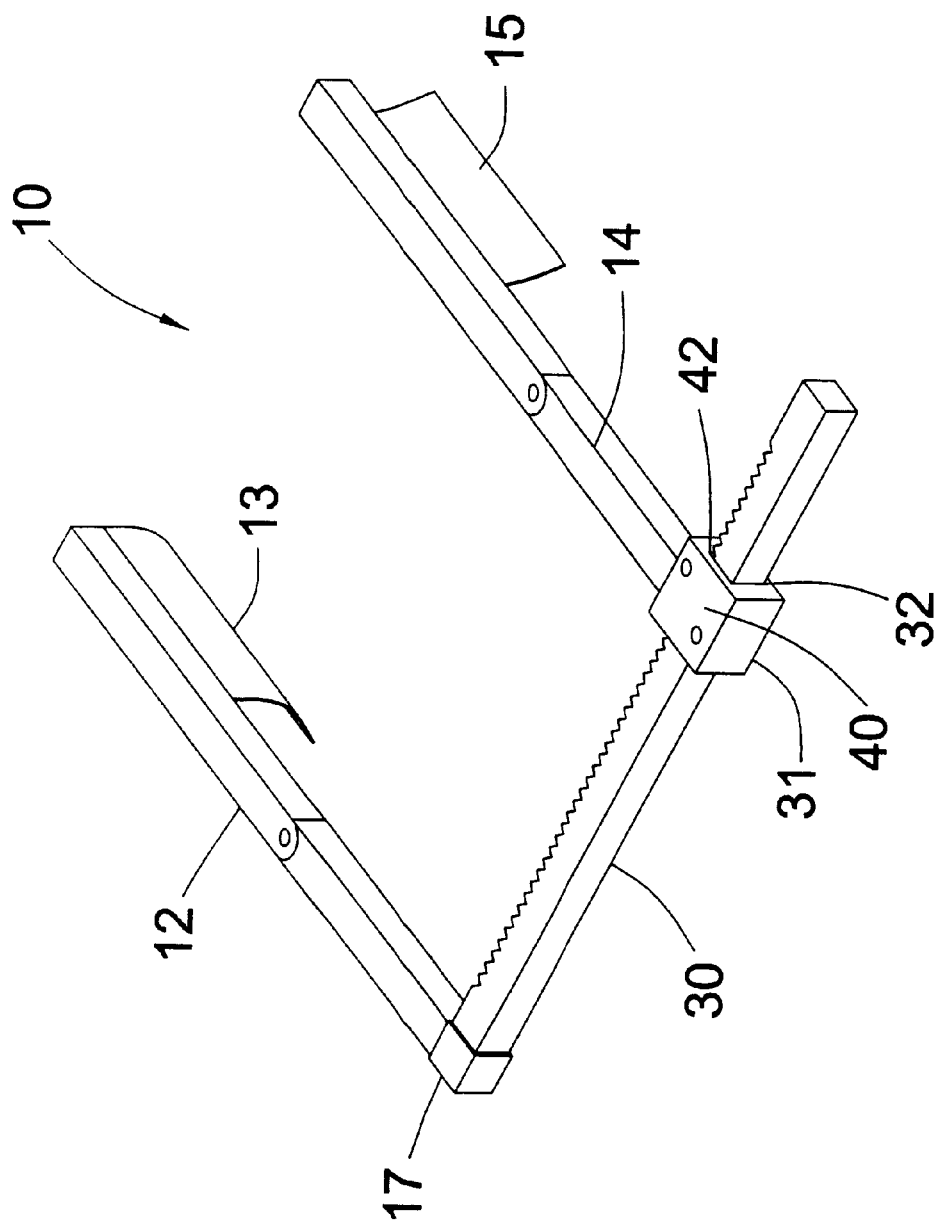
FIG. 1 is a perspective view of a surgical retractor having adjustable arms and gear drive mechanism.
Figure 2:
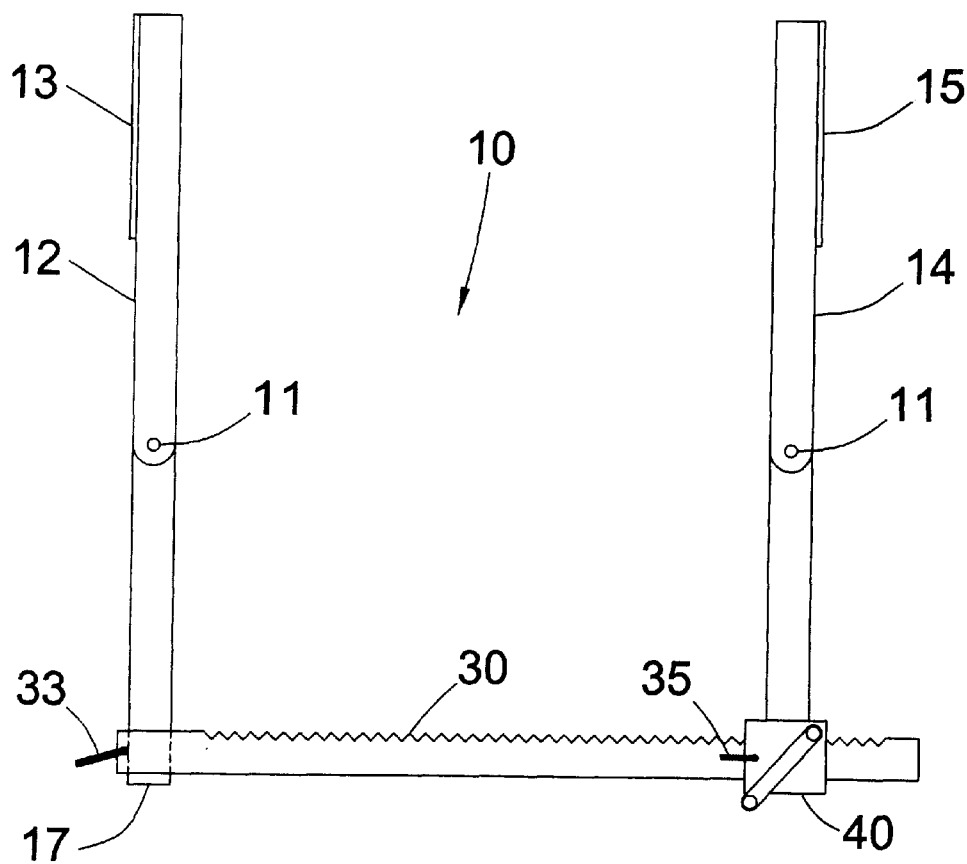
FIG. 2 is a plan view of the surgical retractor of FIG. 1.
Figure 3:
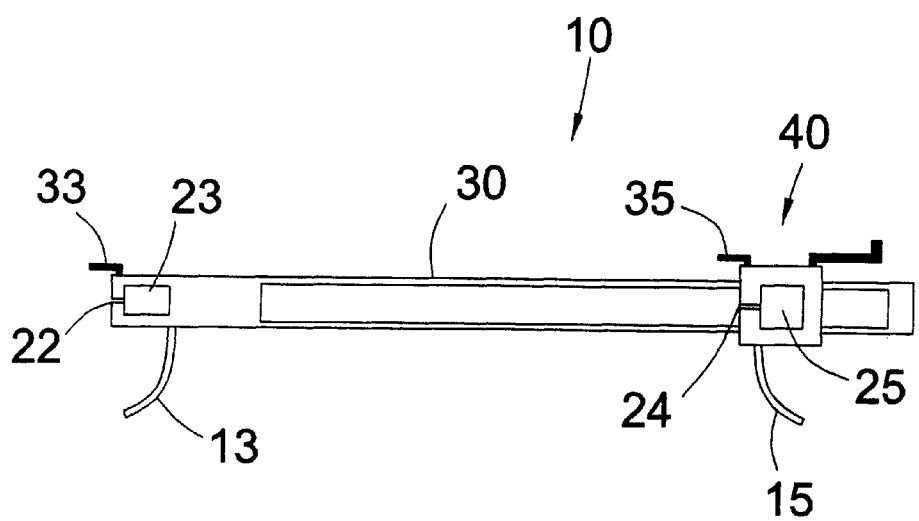
FIG. 3 is a side view of the support rod, clamp assemblies and gear drive mechanism for the surgical retractor of FIG. 1.
Figure 4:
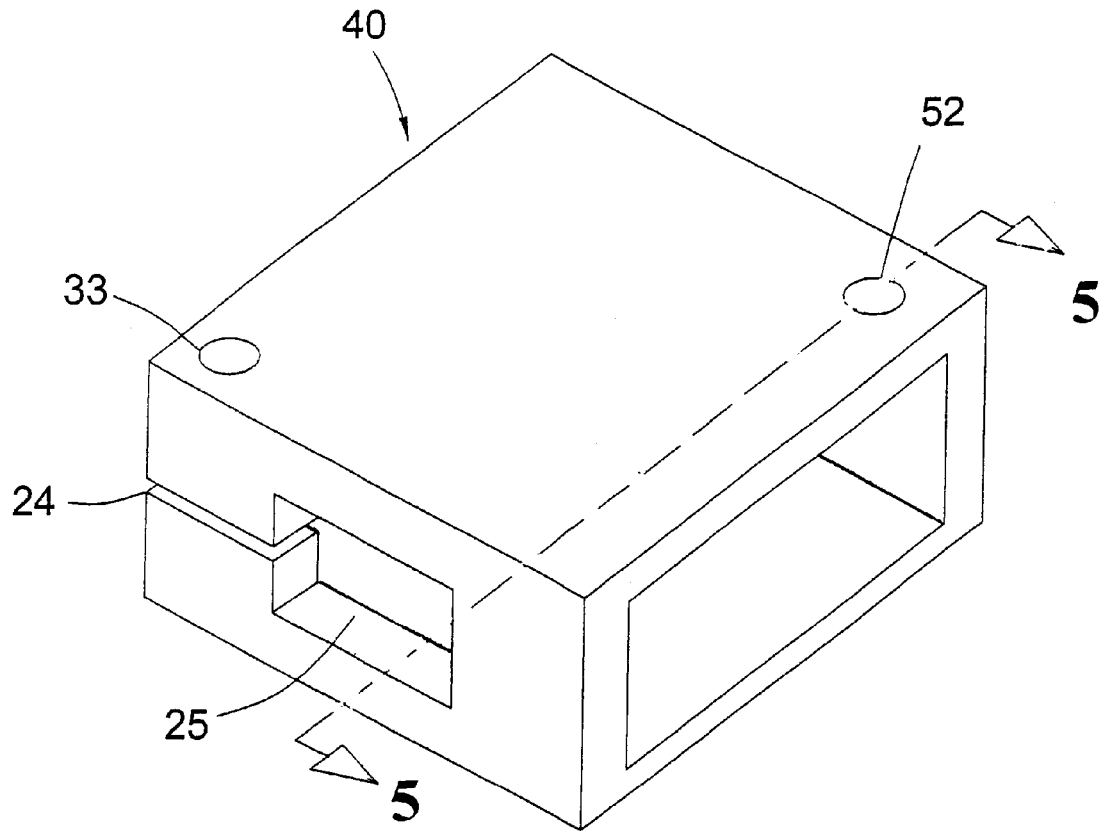
FIG. 4 is a perspective view of the gear drive mechanism for the surgical retractor of FIG. 1.
Figure 5:
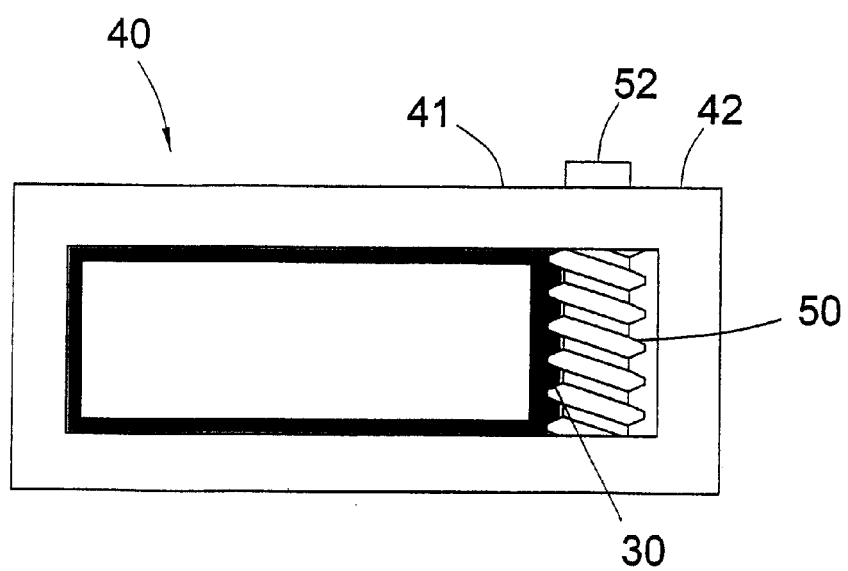
FIG. 5 is cross-sectional view about line 5—5 of FIG. 4 illustrating the worm drive interface with a support rod.

Referring to FIG. 1, surgical retractor 10 comprises retractor arms 12 and 14 which are carried on a retractor crossbar or support shaft 30. Retractor blades 13 and 15 are mounted near the ends of arms 12 and 14. The retractor blades 13 and 15 extend into the incision in communication with the patient's tissue. Blades 13 and 15 are shaped to engage the patient's tissue so that the possibility of slipping is lessened or eliminated. Typically blades 13 and 15 are shaped with a curve such that they may be placed under the patients ribs. The retractor arms 12 and 14 and their blades 13 and 15 may be of a known design. The retractor arms 12 and 14 and support rod 30 have a rectangular or square cross-section. Retractor arm 12 is fixably attached to support rod 30 about distal end 17. Retractor arm 14 slides longitudinally within opening 31 of the retractor arm drive 40. The retractor arm drive 40 includes drive 42, which contains the drive components within the drive housing 40. Opening 32 has a cross-section that is sized to accept support rod 30.

With combined reference to FIGS. 1–5, a worm 50 is rotatably mounted within the drive housing 42 and has upper end 52, which extends through the upper surface 41 of drive housing 42. The upper end of worm 50 has means for receiving a wrench or drive arm. Worm gear 50 threadably engages external threads on support shaft 30. The thread profile is as such to resist the forces that act in a generally longitudinally direction along support rod 30. Other thread profiles may also be used. Rotation of the wrench or handle rotates worm gear 50 on shaft 51, which in turn, causes the drive housing 42 to move in an axial direction along the support shaft 30. The drive housing may also contain a means for locking in addition to the frictional locking caused by the thread pitch.

The length and position of retractor arms can be adjusted by a user. The arms may be rotated about pinned joint 11; and retractor arms 12 and 14 are length adjustable. Arms 12 and 14 are slidably affixed through clamps 22 and 24. Clamps 22 and 24 include openings 23 and 25 having cross-sections sized to accept the cross-section of the respective retractor arms 12 and 14. To operate clamps 23 and 25, bolts 33 and 35 threadably engage respectively into threaded apertures formed in lower portions of clamps 22 and 24. Once arms 12 and 14 are adjusted for length, bolts 33 and 35 are turned clockwise to tighten clamps 22 and 24 which locks arms 12 and 14 into a desired position.

Figure 6:
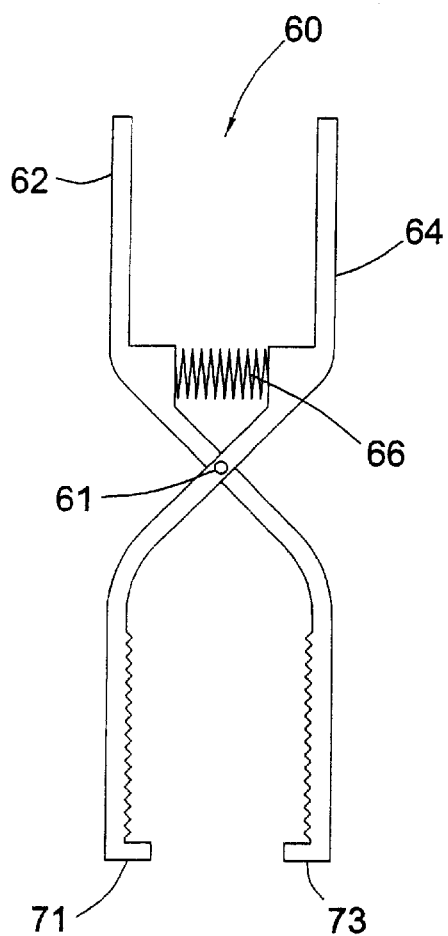
FIG. 6 is a plan view of a connector according to one embodiment of the present invention.

According to the present invention, a variety of connecting mechanisms are provided for detachably connecting medical equipment to an arm of a surgical retractor. More specifically, each connecting mechanism provides a holder for detachably holding the medical equipment at least partially outside a field of surgery defined between the blades of a surgical retractor. FIG. 6 illustrates a connector of this invention that is designed to hold cannula, catheters or tubing to the surface of the surgical retractor. Connector 60 comprises first arm 62, second arm 64, and spring element 66. First arm 62 is connected to second arm 64 by pin 61.

Figure 7:
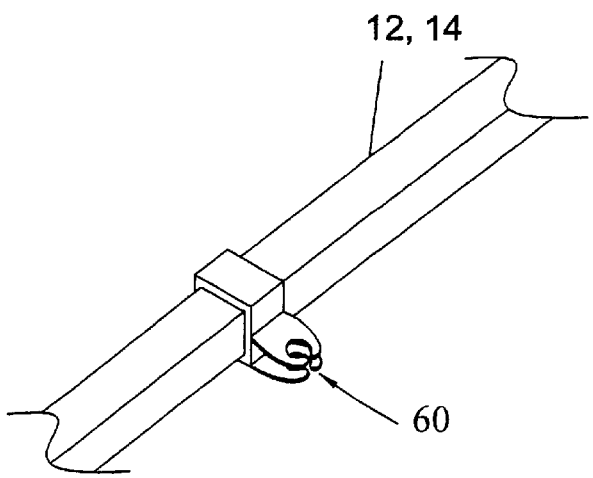
FIG. 7 is a perspective view of the retractor arm having the connector of FIG. 6 attached thereto.

As illustrated in FIG. 7, connector 60 is first inserted over arm 12 or arm 14 of surgical retractor 10 by applying opposing force at distal ends of first arm 62 and second arm 64. After placing connector 60 over arm 12 or 14, the first arm 62 and second arm 64 of connector 60 retract, engaging ridges 71 and 73. Ridges 71 and 73 provide a frictional fit between connector 60 and retractor arm 12 or 14.

Figure 8:
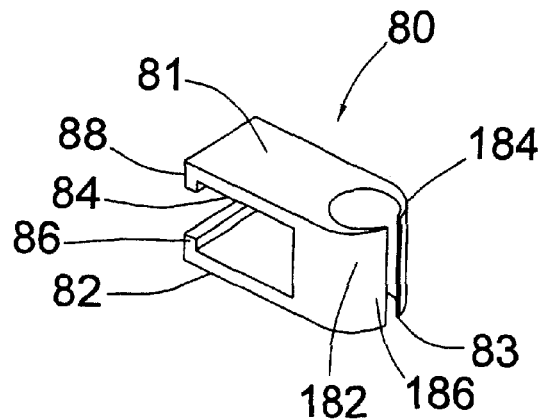
FIG. 8 is a perspective view a connector according to an additional embodiment of the present invention.

A further embodiment as illustrated in FIG. 8 connector 80 comprises one or more springably resilient surfaces. Connector 80 is constructed of a flexible polymer which can be deformed though will retain its initial shape. Connector 80 includes first and second coupler arms 82,84 for coupling the connector 80 to a retractor arm, and a holder 83 comprising first and second holder arms 182,184 for holding medical equipment therebetween. First and second coupler arms 82,84 are constructed of a springably flexible material, having distal connector ends 86,88 shaped to slide over and become detachably affixed to arm 12 or 14 of surgical retractor 10. Holder 83 detachably grasps medical devices for transferring blood, such as tubing, cannulas and blood pumps. Holder 83 comprises arms 182 and 184 constructed of a resilient material that forms around the device when a device is placed into the holder 83. Connector 80 is first placed over arm 12, 14 of surgical retractor 10. Once in place, a cannula, tubing or blood pump is then pushed into arms 182 and 184 which deflect around the item until it is fully inserted into holder 83. The arms 182 and 184 hold the cannula in place.

Connector 80 contains means for frictionally engaging a second surface. Connector 80 is placed over retractor arms 12 and 14 by applying a force to connector 80 perpendicular to surface 81 of connector 80. Coupler arms 82 and 84 are deformed around retractor arms 12 and 14 from the applied force. Once fully engaged on retractor arm 12 or 14, coupler arms 82 and 84 retract around retractor arm 12 or 14 providing a frictional fit. Once connector 80 is engaged about the retractor arm 12 or 14, a medical device or instrument can be inserted into holder 83 located on distal end of connector 80.

Figure 9:
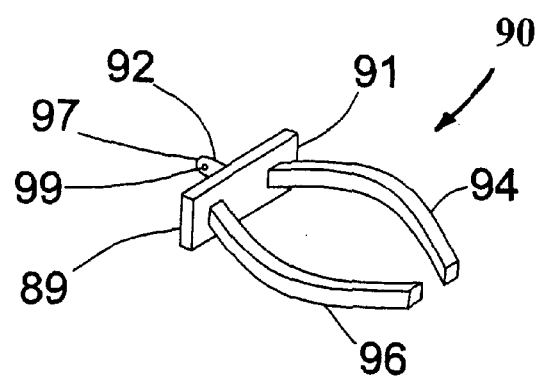
FIG. 9 is the perspective view of a connector according to still another embodiment of the present invention.
Figure 10:
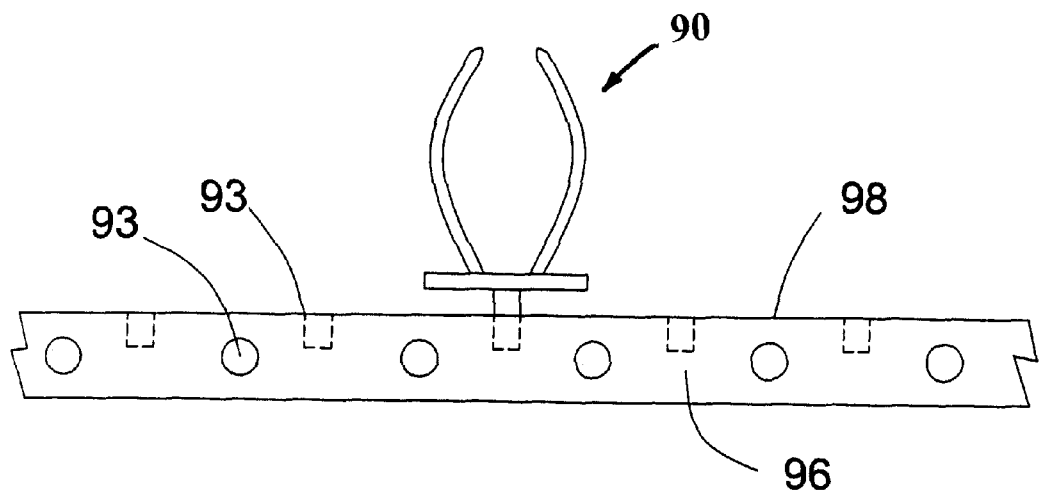
FIG. 10 is a side view illustrating the connector FIG. 9 being inserted onto an arm of the surgical retractor.

According to another embodiment of the present invention, mounting apertures may be formed in the retractor arm and a connecting mechanism provided capable of engaging with the mounting apertures to detachably couple medical equipment to the retractor arm. As shown in FIG. 10, arms 12 and 14 of surgical retractor 10 are constructed having a square or rectangular cross-sectional area. Arms 12 and 14 contain mounting apertures or holes 93 that are approximately centered about surface 96 and surface 98. With combined reference to FIGS. 9 and 10, a connector 90 according to this embodiment is provided comprising a of base 91, locking pin 92 and flexible holder arms 94 and 96. Holder arms 94 and 96 may be constructed of a resilient material such as plastic or metal. Alternatively, holder arms 94 and 96 may be constructed of an easily deformable material so that the holder arms 94 and 96 may be easily shaped to accommodate various surgical devices for transferring fluids. Locking pin 92 extends from distal surface 89 of base plate 91. Distal end 97 of locking pin 92 contains a locking means 99 for locking pin 92 to holes 93 located about arms 12 and 14 of surgical retractor 10. As illustrated in FIG. 10, pin 92 is inserted into hole 93 located on arm 12 and 14. When fully inserted, locking means 99 is deployed, thereby locking connector 90 to arm 12 or 14 of the surgical retractor 10. Surgical devices for transferring fluids such as tubing, cannula, catheters, or a blood pump can then be held by arms 94 and 96 of connector 90.

Figure 11:
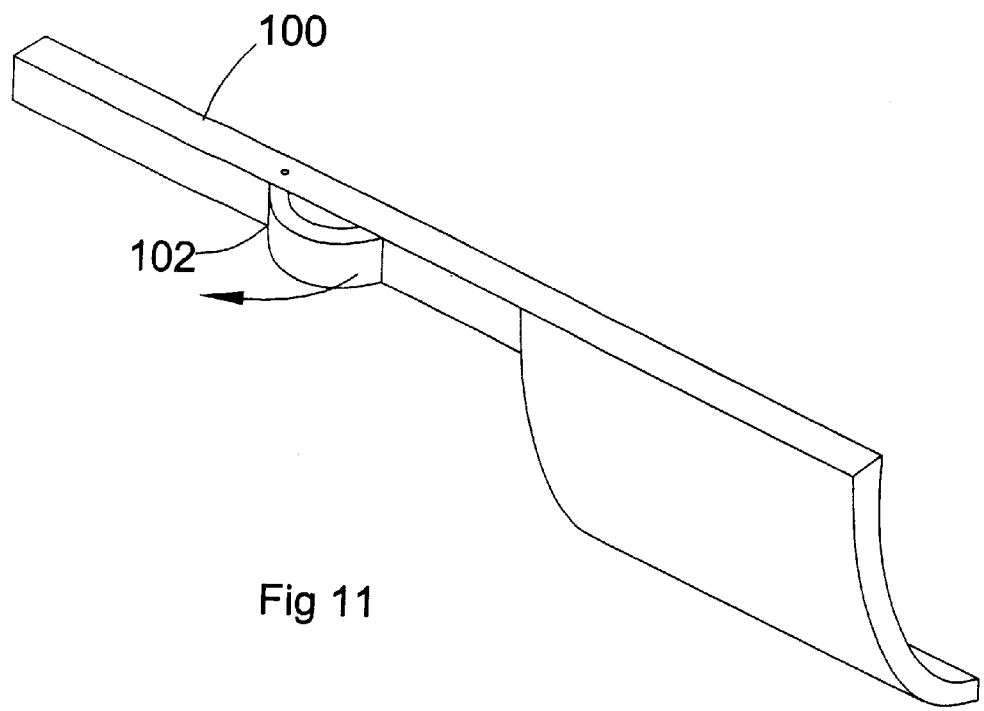
FIG. 11 is a perspective view of a connector according to a still further embodiment of the present invention.

A still further aspect of the present invention involves forming a connecting mechanism as part of the retractor arm itself, Referring to FIG. 11, the connecting mechanism of this embodiment comprises a holder arm 102 coupled to the retractor arm 100 via pin member. Holder arm 102 is preferably spring loaded such that it may be selectively moved away to allow the medical devices for transferring fluid, such as tubing, cannula, or blood pump, to be positioned next to the retractor arm 100. The holder arm 102 moves under the action of the spring to hold the tubing, cannula or blood pump in position against the arm 100.

Figure 12:
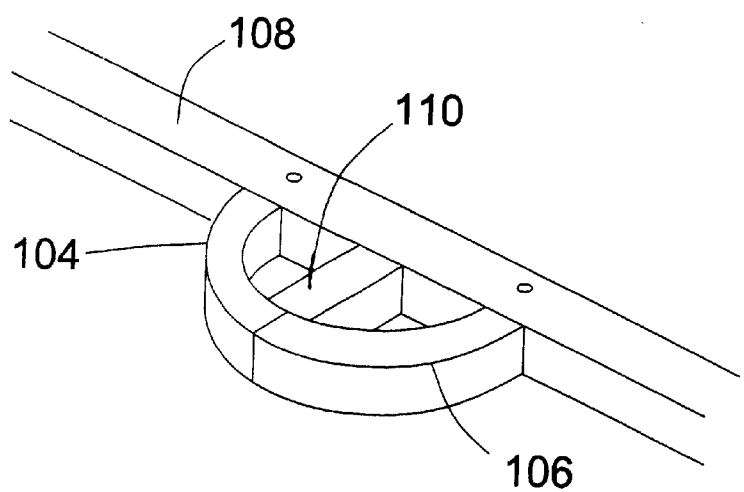
FIG. 12 is a perspective view of a connector according to another embodiment of of the present invention.

FIG. 12 shows an alternate embodiment with two spring loaded holder arms 104 and 106 separated by bar 110 connected to the arm 108. In this manner, two different items can be positioned against the arm 108.

Figure 13A:
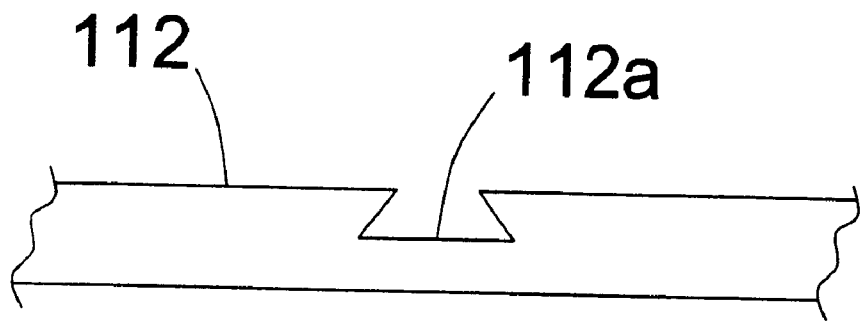
FIG. 13A illustrates a portion of the surgical retractor arm having a dovetail receiving portion.
Figure 13B:
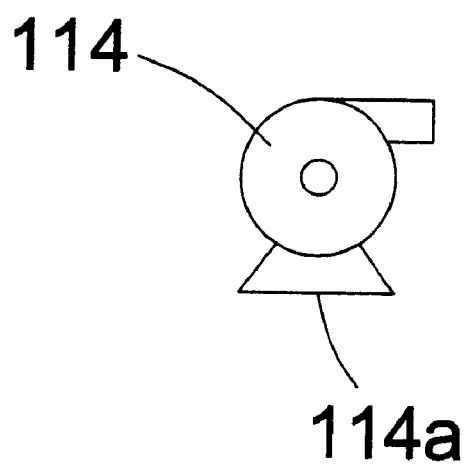
FIG. 13B is a diagram illustrating a blood pump having a dovetail mating portion for slidably engaging with the dovetail receiving portion formed in the surgical retractor arm.
Figure 14:
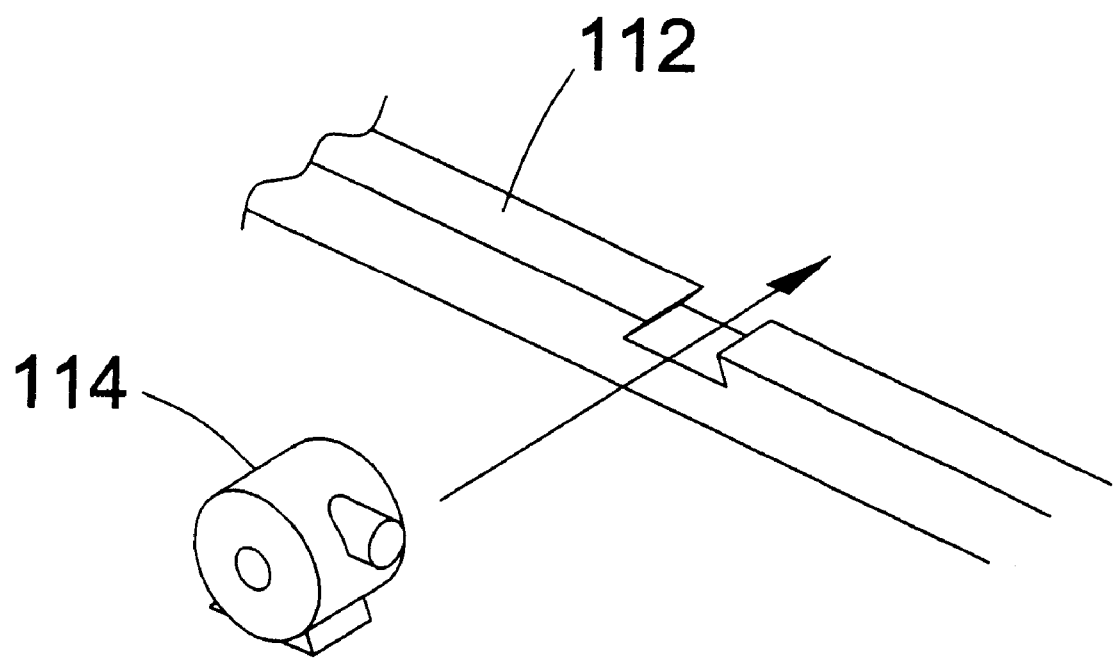
FIG. 14 is a perspective view of the blood pump of FIG. 13B and surgical retractor arm of FIG. 13A being connected together.

FIGS. 13 and 14 show an alternate embodiment in which the surgical retractor arm has a removed region capable of receiving a mating element or portion formed or connected to medical equipment such as a blood pump, tubing, or cannula. FIG. 13A is a diagram showing a portion of a retractor arm 112 having a female dovetail slot 112a. In FIG. 13B, the blood pump 114 includes a male dovetail portion 114a. The male dovetail portion 114a connects with the female dovetail slot 112a on the retractor arm 112 so that the blood pump 114 can be held away from the surgeon's field of operation. FIG. 14 is a perspective view showing the blood pump 114 connecting to the retractor arm 112. In a preferred embodiment, the blood pump 114 is of the type described in patent application U.S. Ser. No. 08/933,566, filed on Sep. 19, 1997, which is incorporated herein by reference.

Figure 15A:
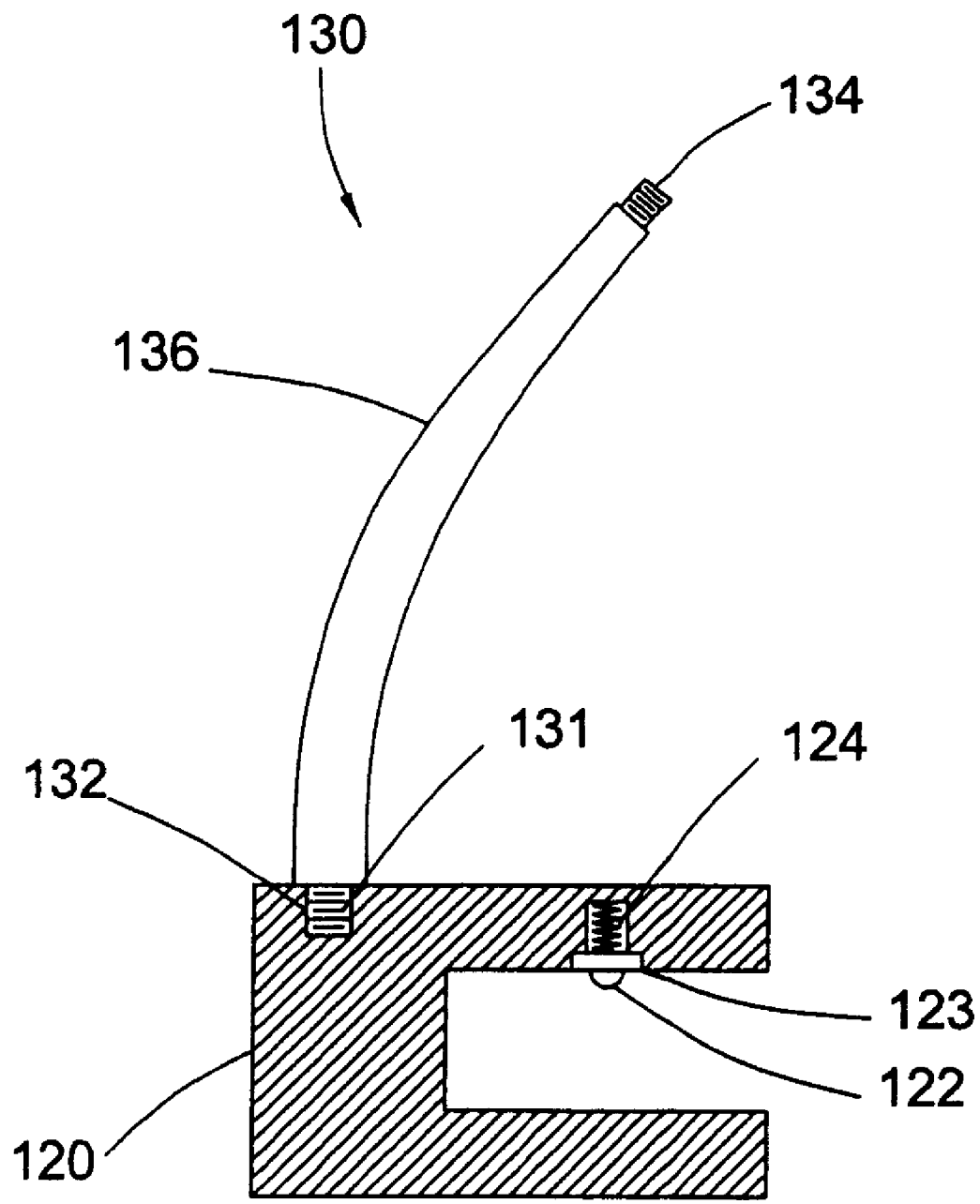
FIG. 15A is a diagram of a connector of one embodiment of the present invention having a coupler block for coupling to a retractor arm and an elongated flexible arm.
Figure 15C:
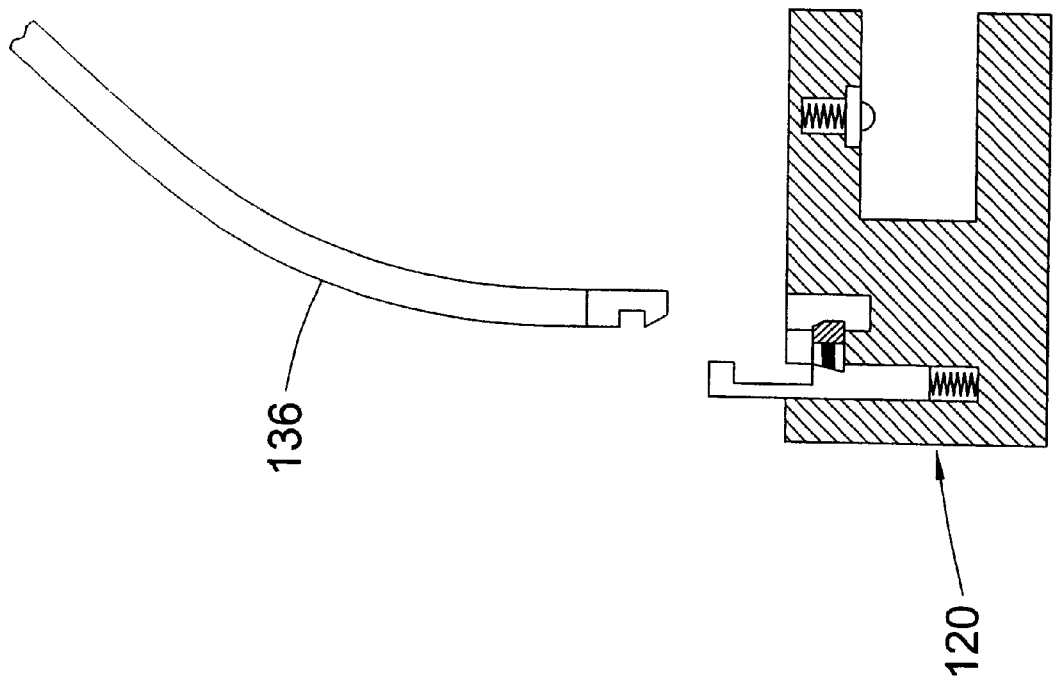
FIGS. 15C and 15D are diagrams illustrating the various methods of coupling an elongated flexible arm of the type shown in 15A to a coupler block of the type shown in FIG. 15A in accordance with a further embodiment of the present invention.
Figure 15B:
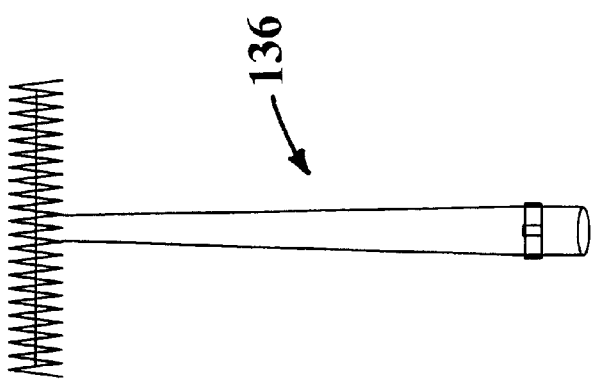
FIG. 15B is a diagram of a connector of another embodiment of the present invention having an elongated flexible arm with a suture holder coupled thereto.

A still further embodiment of the present invention involves providing a connection mechanism having an elongated flexible member coupled to the retractor arm. As shown in FIG. 15A, an elongated flexible memeber 136 may be attached to a coupler block 130. Coupler block 130 is adapted to be received on retractor 10. Coupler block 130 contains threaded means 132 adapted to receive flexible arm 136. Coupler block 130 also includes means for detachably attaching to retractor 10. In one embodiment, as illustrated in FIG. 15A, ball 122 engages apertures 93 on retractor 10 as illustrated in FIG. 10. Ball 122 is further held in place by retainer ring 123 and spring means 124. FIG. 15B is a diagram of an alternate embodiment where the flexible arm 136 connects directly with the hole 93 in the surgical retractor arm. Looking again at FIG. 15A, flexible arm 136 contains first end 131 which is adapted to threadably engage aperture 132 on coupler block 120. Second end 134 is adapted to threadably engage holder arrangements such as those illustrated in FIGS. 16–20.

Figure 15D:
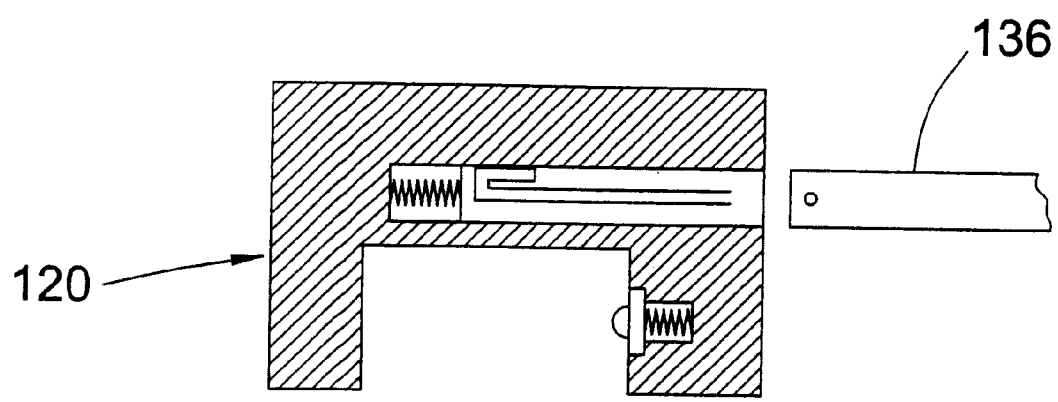

The flexible arm 136 can also be attached to coupler block 120 with other methods. As shown in FIGS. 15C and 15D, in an alternate method, a spring loaded locking mechanism is used that works by inserting and twisting the flexible arm 136 into the coupler block 120.

Figure 17:
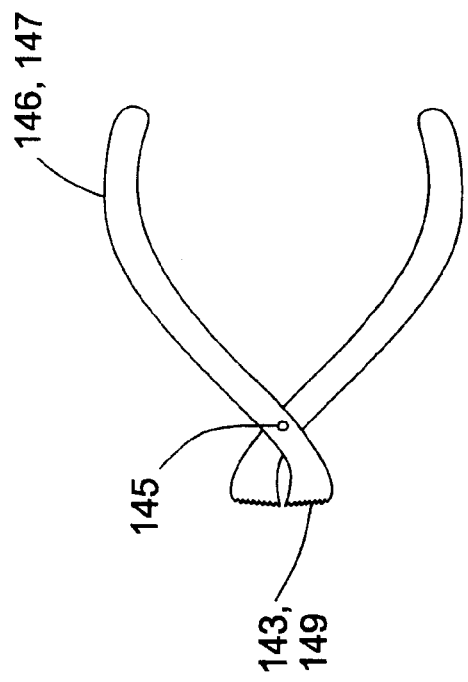
FIG. 17 is a diagram of a holder arm of the type shown in FIG. 16 with teeth for engaging with a toothed portion within the coupler block of FIG. 16 with teeth.
Figure 16:
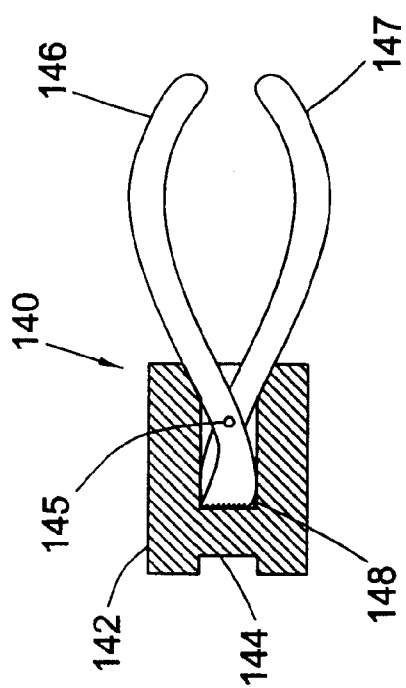
FIG. 16 is a diagram of a holder forming part of a connector of the present invention the holder having a block and a pair of holder arms for receiving medical equipment therebetween.

A variety of holder arrangements may be provided for use with the flexible arm memeber described above. For example, with reference to FIG. 16, a holder 140 is provided adapted to receive various medical devices used during surgical procedures. Holder 140 contains means for engaging 144 flexible shaft 136 as illustrated in FIG. 15. Further Holder 140 contains holder arms 146 and 147 which are adapted to receive surgical devices. Arms 146 and 147 pivot about pin 145. As shown in FIG. 17, distal ends 143 and 149 may have teeth 143 and 149 which engage means for locking arms 146 and 147 in holder block 142.

Figure 18:
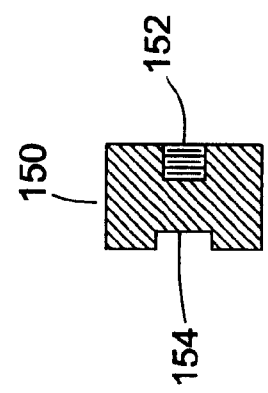
FIG. 18 is a diagram of a a holder forming part of a connector of the present invention, the holder being equipped with a magnet for magnetically holding medical equipment.

In another aspect, as illustrated in FIG. 18, a holder 150 is adapted to receive various surgical instruments. In the preferred embodiment, holder 150 contains a magnet 152 and a region 154 for connection to the flexible shaft 136.

Figure 19:
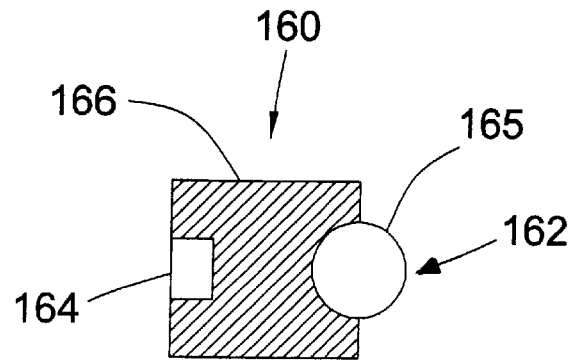
FIG. 19 is a side view of a suture holder for use with a connector of the present invention.
Figure 20:
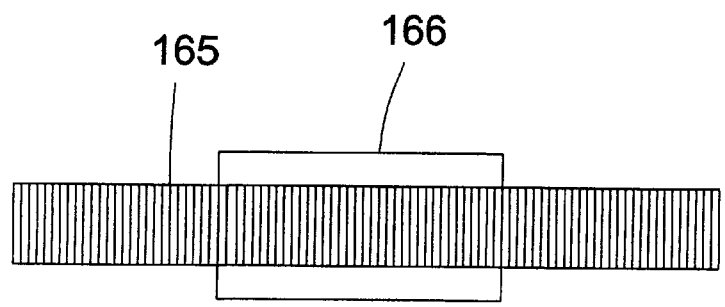
FIG. 20 is a front view of the suture holder of FIG. 19.
Figure 22:
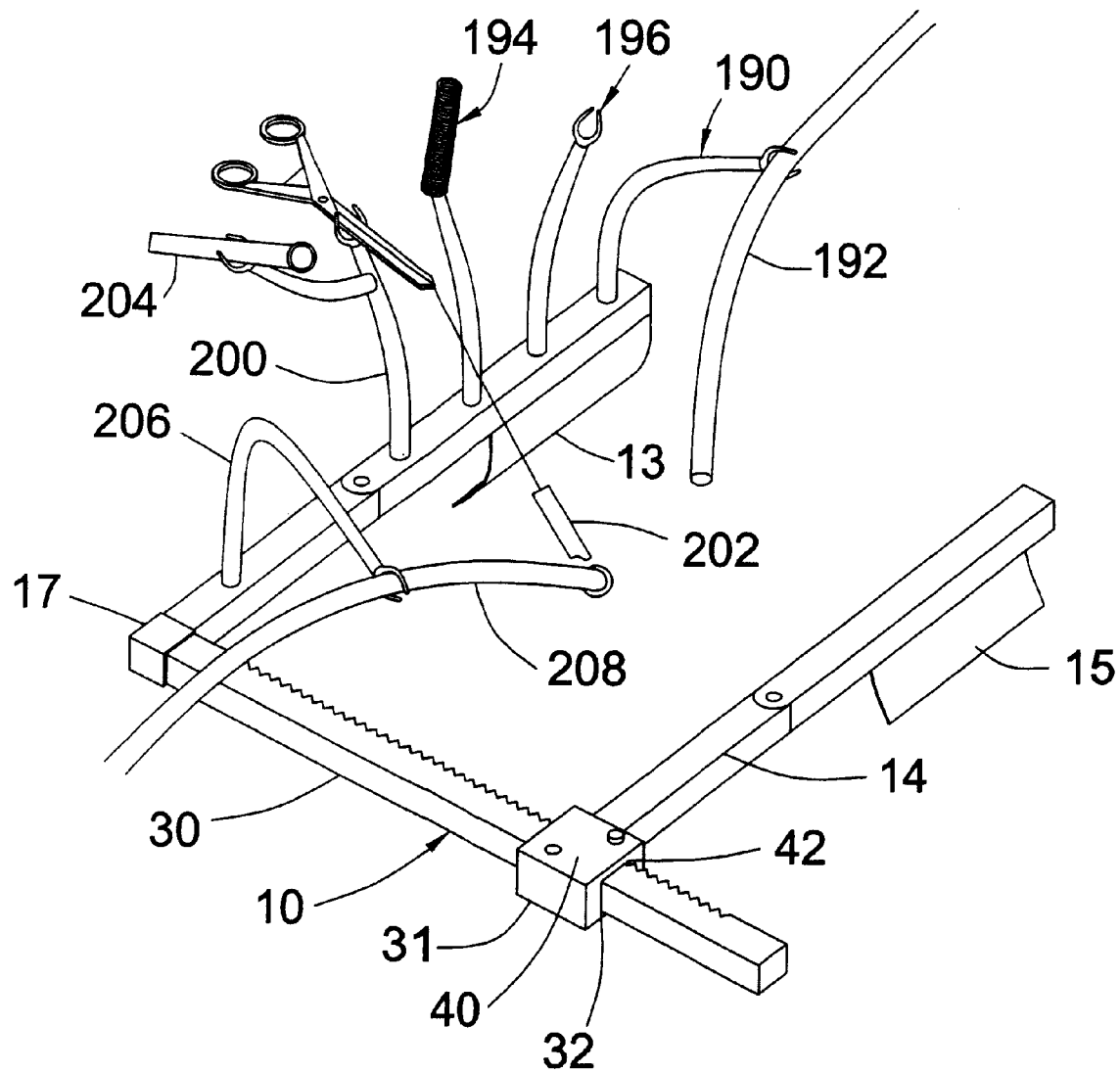
FIG. 22 is a diagram of a surgical retractor with some of the connectors of the present invention attached.
Figure 23:
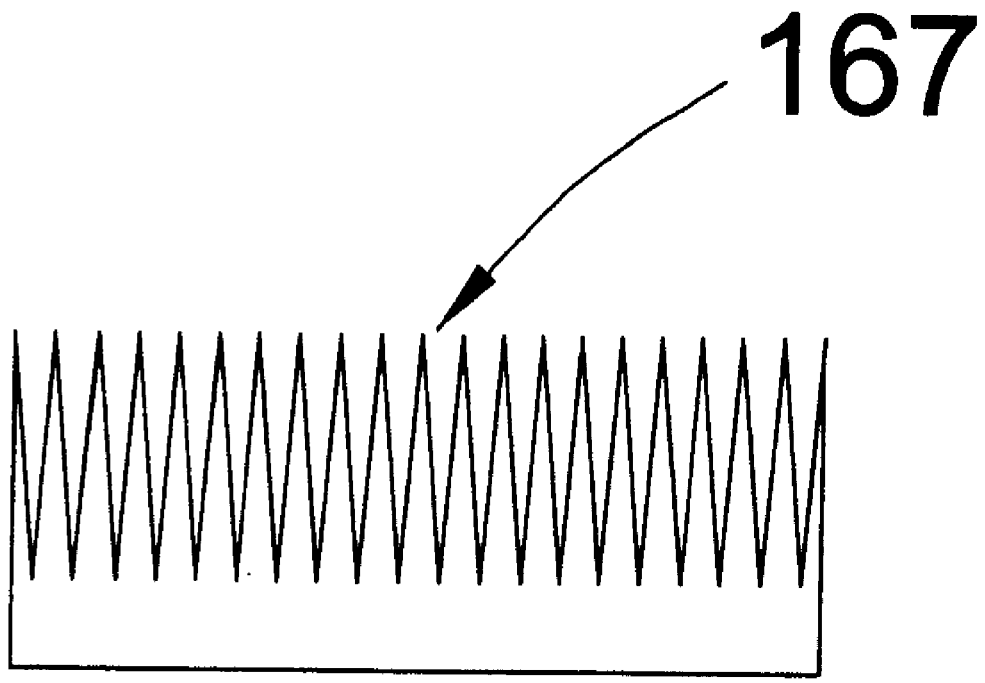
FIG. 23 is a diagram of a suture holder for use with a connector of the present invention.

In another aspect, as illustrated in FIG. 19 a holder 160 is adapted to receive various surgical suture. Holder 160 includes a suture holding element 162 couple to a holder block 166. The holder block 166 further contains means 164 for adapting suture device to flexible shaft 136. The suture holding element 162 may comprise any number of devices suitable for detachably retaining a suture therein, such as the spring element 165 shown in FIGS. 19 and 20 or a suture holder block 167 as shown in FIG. 23. The suture holder element 162 may be coupled to the flexible arm 136 which, in turn, can be attached directly within receiving apertures 93 formed in the retractor arm (as shown in FIG. 22) or attached to the retractor 10 by utilizing coupler block 120. During surgical procedures that require sutures, many times one end of the suture is held by an assistant in the surgical room. The present invention allows the physician to hold the free end of a suture without the need of another person within the surgical room. Typically the device of the present invention can be utilized during anastomosis procedures. Further, the suture holder can be used during heart valve surgery. As shown in FIG. 23, the suture holder can also be in the form of a flexible device having slots which are adapted to receive sutures.

Figure 21:
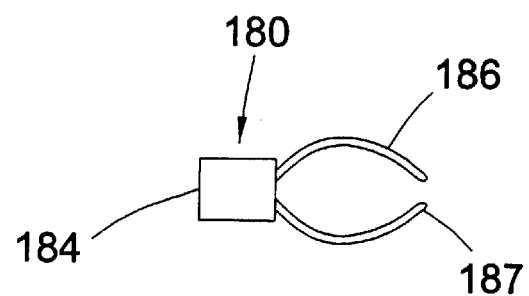
FIG. 21 is a diagram of a connector of the present invention.

In another aspect, as illustrated in FIG. 21, a holder 180 may be provided formed of an material having elastic properties. Holder 180 is adapted to engage the distal end of flexible shaft 136. Holder 180 includes holder arms 186 and 187 that are adapted to receive various surgical devices. In use holder 180 is attached to distal end of flexible shaft 136. When the surgeon desires to hold a device during surgery the holder 180 is positioned and the device is inserted through arms 186 and 187 which flexibly engage the device.

FIG. 22 is a diagram that illustrates the use of some of the connectors of the present invention with a surgical retractor 10. Connector 190 holds a cannula 192 in place. An instrument holder 196 and suture holder 194 are also shown. Connector 200 holds a tourniquet 202 and field-of-surgery light 204. Connector 206 holds suction tube 208.

While the present invention has been described with reference to the aforementioned application, this description of the preferred embodiment and method is not meant to be construed in a limiting sense. It should be understood that all aspects of the present invention are not limited to the specific depictions, configurations, or relative proportions set forth herein which depend upon a variety of conditions.

Various modifications in form and detail of the various embodiments of the disclosed invention, as well as other variations of the present invention, will be apparent to a person skilled in the art upon reference to the present disclosure. It is therefore contemplated that all attendant claims shall cover any such modifications or variations of the described embodiments as following within the true spirit and scope of the present invention.

What is claimed is:

1. A surgical retractor, comprising:

first and second retractor arms connected to a support shaft;

first and second retractor blades respectively attached to said first and second retractor arms for retracting tissue during surgery; and a connector coupled to at least one of said retractor arms for connecting medical equipment used during surgical procedures to said retractor arm, said connector including a holder for detachably holding said medical equipment at least partially outside a field of surgery defined between said first and second retractor blades.

2. The surgical retractor of claim 1, wherein said holder comprises at least one holder arm resiliently biased to detachably hold said medical equipment.

3. The surgical retractor of claim 1, wherein said holder comprises a magnet for magnetically holding said medical equipment.

4. The surgical retractor of claim 1, wherein said holder comprises a suture holder having a plurality of grooves for detachably holding sutures.

5. The surgical retractor of claim 3, said connector including an elongated flexible member having a first end coupled to said retractor arm, and a second end coupled to said magnet.

6. The surgical retractor of claim 4, said connector including an elongated flexible member having a first end coupled to said retractor arm, and a second end coupled to said suture holder.

7. The surgical retractor of claim 2, wherein said at least one holder arm is hingedly coupled to said retractor arm.

8. The surgical retractor of claim 2, wherein said holder comprises a first holder arm and a second holder arm adapted to detachably receive said medical equipment therebetween.

9. The surgical retractor of claim 8, wherein said first and second holder arms are coupled to said retractor arm by a pair of coupler arms positioned at least partially around the cross section of said retractor arm.

10. The surgical retractor of claim 8, wherein said first and second holder arms are coupled to said retractor arm by an elongated flexible member.

11. The surgical retractor of claim 8, wherein said first and second holder arms are coupled to said retractor arm by an engagement pin dimensioned to be detachably positioned within a receiving aperture formed in said retractor arm.

12. The surgical retractor of claim 8, wherein said first and second holder arms have teeth portions which engage within a holder block to lock said first and second holder arms about said medical equipment.

13. The surgical retractor of claim 1, wherein said connector comprises a dovetail receiving portion formed in at least one of said first and second retractor arms for slidably receiving a dovetail mating portion on said medical equipment.

14. The surgical retractor of claim 13, wherein said dovetail receiving portion is adapted to receive a dovetail mating portion coupled to a blood pump.

15. The surgical retractor of claim 1, wherein said holder is adapted to receive a cannula.

16. A method of facilitating surgery, comprising the steps of:

(a) providing a surgical retractor having a first retractor arm and a second retractor arm connected to a support shaft, a retractor blade attached to each of said first and second retractor arms for retracting tissue during surgery, and a connector coupled to at least one of said retractor arms for connecting medical equipment used during surgical procedures to said retractor arm, said connector including a holder for detachably holding said medical equipment at least partially outside a field of surgery defined between said first and second retractor blades;

(b) spreading an opening formed in a patient by placing said retractor blades of said surgical retractor inside said opening and moving said first and second retractor arms apart; and (c) detachably engaging medical equipment used during surgery to said holder of said connector such that said medical equipment may be maintained at least partially outside said field of surgery.

17. The method of claim 16, step (a) including the sub-step of providing said holder comprising at least one resiliently biased holder arm, and step (c) including the sub-step of resiliently biasing said at least one holder arm to detachably hold said medical equipment.

18. The method of claim 16, step (a) including the sub-step of providing said holder comprising a magnet, and step (c) including the sub-step of using said magnet to detachably hold said medical equipment.

19. The method of claim 16, step (a) including the sub-step of providing said holder comprising a suture holder having a plurality of grooves, and step (c) including the sub-step of detachably positioning sutures within said grooves.

20. The method of claim 16, step (a) including the sub-step of providing said connector comprising a dovetail receiving portion formed in at least one of said first and second retractor arms, and step (c) including the sub-step of slidably engaging a dovetail mating portion on said medical equipment within said dovetail receiving portion.

21. The method of claim 18, step (a) including the sub-step of providing said connector comprising an elongated flexible member having a first end coupled to said retractor arm, and a second end coupled to said magnet.

22. The method of claim 19, step (a) including the sub-step of providing said connector comprising an elongated flexible member having a first end coupled to said retractor arm, and a second end coupled to said suture holder.

23. The method of claim 17, step (a) including the sub-step of providing said connector comprising at least one holder arm hingedly coupled to said retractor arm.

24. The method of claim 17, step (a) including the sub-step of providing said connector comprising a first holder arm and a second holder arm adapted to receive said medical equipment therebetween.

25. The method of claim 24, step (a) including the sub-step of coupling said first and second holder arms to said retractor arm with a pair of coupler arms positioned at least partially around the cross section of said retractor arm.

26. The method of claim 24, step (a) including the sub-step of coupling said first and second holder arms to said retractor arm with an elongated flexible member.

27. The method of claim 24, step (a) including the sub-step of coupling said first and second holder arms to said retractor arm with an engagement pin dimensioned to be detachably positioned within a receiving aperture formed in said retractor arm.

28. The method of claim 24, step (a) including the sub-step of providing said first and second holder arms with teeth portions which engage within a holder block to detachably lock said first and second holder arms about said medical equipment.

29. A connector for connecting medical equipment to a retractor arm of a surgical retractor, said surgical retractor having first and second retractor arms coupled to a support shaft, and first and second retractor blades respectively attached to said first and second retractor arms for retracting tissue during surgery, said connector comprising:

a holder for detachably holding said medical equipment at least partially outside a field of surgery defined between said first and second retractor blades.

30. The connector of claim 29, wherein said holder comprises at least one holder arm resiliently biased to detachably hold said medical equipment.

31. The connector of claim 29, wherein said holder comprises a magnet for magnetically holding said medical equipment.

32. The connector of claim 29, wherein said holder comprises a suture holder having a plurality of grooves for detachably holding sutures.

33. The connector of claim 31, said connector including an elongated flexible member having a first end coupled to said retractor arm, and a second end coupled to said magnet.

34. The connector of claim 32, said connector including an elongated flexible member having a first end coupled to said retractor arm, and a second end coupled to said suture holder.

35. The connector of claim 30, wherein said at least one holder arm is hingedly coupled to said retractor arm.

36. The connector of claim 30, wherein said holder comprises a first holder arm and a second holder arm adapted to detachably receive said medical equipment therebetween.

37. The connector of claim 36, wherein said first and second holder arms are coupled to said retractor arm by a pair of coupler arms positioned at least partially around the cross section of said retractor arm.

38. The connector of claim 36, wherein said first and second holder arms are coupled to said retractor arm by an elongated flexible member.

39. The connector of claim 36, wherein said first and second holder arms are coupled to said retractor arm by an engagement pin dimensioned to be detachably positioned within a receiving aperture formed in said retractor arm.

40. The connector of claim 36, wherein said first and second holder arms have teeth portions which engage within a holder block to lock said first and second holder arms about said medical equipment.

41. The connector of claim 29, wherein said connector comprises a dovetail receiving portion formed in at least one of said first and second retractor arms for slidably receiving a dovetail mating portion on said medical equipment.

42. The connector of claim 41, wherein said dovetail receiving portion is adapted to receive a dovetail mating portion coupled to a blood pump.

43. The connector of claim 29, wherein said holder is adapted to receive a cannula.

* * * * *